(12) United States Patent
Evans et al.

(10) Patent No.: US 6,391,847 B1
(45) Date of Patent: May 21, 2002

(54) METHOD, POLYPEPTIDES, NUCLEOTIDE SEQUENCE OF XOR-6, A VITAMIN D-LIKE RECEPTOR FROM XENOPUS

(75) Inventors: Ronald M. Evans, La Jolla; Bruce Blumberg, San Diego, both of CA (US); Kazuhiko Umesono, Nara (JP)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 08/875,082

(22) PCT Filed: Jan. 16, 1996

(86) PCT No.: PCT/US96/00058

§ 371 Date: Jul. 17, 1997

§ 102(e) Date: Jul. 17, 1997

(87) PCT Pub. No.: WO96/22390

PCT Pub. Date: Jul. 25, 1996

Related U.S. Application Data (63) Continuation-in-part of application No. 08/374,445, filed on Jan. 17, 1995, now abandoned.

(51) Int. Cl.[7] .............................................. A01N 37/18
(52) U.S. Cl. ........................... 514/2; 514/569; 514/617
(58) Field of Search ................................. 514/569, 617; 530/350; 435/320.1

(56) References Cited

U.S. PATENT DOCUMENTS

| | | | |
|---|---|---|---|
| 4,981,784 A | 1/1991 | Evans et al. | ..................... 435/6 |
| 5,312,732 A | * 5/1994 | Evans et al. | ................ 435/69.1 |
| 5,668,175 A | 9/1997 | Evans et al. | ................ 514/569 |

OTHER PUBLICATIONS

Evans, R. M., "The steroid and Thyroid Hormone Super Family" *Science* 240: 889–895 (1988).
Hardwood et al. "Identificationof the pcaRKF Gene Cluster from *Pseudomonas putida*: Involvement in Chemotaxis, Biodegradation, and Transport of 4–Hydroxybenzoate" *J. Bacterio.* 176: 6479–6488 (1994).

(List continued on next page.)

*Primary Examiner*—Ardin H. Marschel
(74) *Attorney, Agent, or Firm*—Stephan E. Reiter; Teresa Spehar; Foley & Lardner (57) ABSTRACT

In accordance with the present invention, there are provided new members of the steroid receptor superfamily of receptors, a representative member of which has been designated XOR-6. Invention receptors are responsive to hydroxy, mercapto or amino benzoates, and are expressed, for example, in *Xenopus laevis* embryos. XOR-6 is most closely, although distantly, related to the vitamin D3 receptor (VDR). The proteins are about 73% identical in amino acid sequence in the DNA-binding domains and about 42% identical in the ligand binding domain. Like VDR, XOR-6 has an extended D region between the DNA and ligand binding domains. Notably, the region amino-terminal to the XOR-6 DNA-binding domain is extremely acidic. This may influence its ability to activate target genes. XOR-6 is not restricted to Xenopus because southern blots show the presence of XOR-6-related sequences in a variety of other vertebrates. Indeed, a human genomic clone for an XOR-6 related gene has recently been isolated. In accordance with a particular aspect of the present invention, there are also provided nucleic acid sequences encoding the above-identified receptor, as well as constructs and cells containing same, and probes derived therefrom. Furthermore, we have also discovered that hydroxy, mercapto or amino benzoates modulate the transcription activating effects of invention receptors.

22 Claims, 3 Drawing Sheets

OTHER PUBLICATIONS

Mangelsdorf and Evans, "The RXR Heterodimers and Orphan Receptors" *Cell* 83: 841–850 (1995).

Marder et al., "Blockade of Human Neutrophil Activation by 2-[2-propyl-3-[3-[2-ethyl-4-4(4-fluorophenyl)-5-hydroxyphenoxy]propoxy]phenoxy]benzoic acid (L293111), A Novel Leukotriene $B_4$ Receptor Antagonist" *Biochem. Pharm.* 49:1683–1690 (1995).

McDonnell et al., "Functional Domains of the Human Vitamin $D_3$ Receptor Regulate Osteocalcin Gene Expression" *Molecular Endocrinology* 3: 635–644 (1989).

Smith et al., "A novel nuclear receptor superfamily member in Xenopus that associates with RXR, and shares extensive sequence similarity to the mammalian vitamin D3 receptor" *Nucleic Acids Research* 22: 66–71 (1994).

Charpentier et al., J. Med. Chem., vol. 38, pp. 4993–5006, 1995.*

Laudet et al., The EMBO Journal, vol. 11, No. 3, pp. 1003–1013, 1992.*

* cited by examiner

METHOD, POLYPEPTIDES, NUCLEOTIDE SEQUENCE OF XOR-6, A VITAMIN D-LIKE RECEPTOR FROM XENOPUS

This application is a filing under 35 U.S.C. §371 from PCT/US96/00058, filed Jan. 16, 1996; which is a continuation-in-part and claims priority to U.S. patent application Ser. No. 08/374,445; filed Jan. 17, 1995, now abandoned.

FIELD OF THE INVENTION

The present invention relates to intracellular receptors, and ligands therefor. In a particular aspect, the present invention relates to methods for the modulation of processes mediated by invention receptors, as well as methods for the identification of compounds which effect such modulation.

BACKGROUND OF THE INVENTION

Nuclear receptors constitute a large superfamily of ligand-activated transcription factors. Members of this family influence transcription either directly, through specific binding to the promoters of target genes (see Evans, in *Science* 240:889–895 (1988), or indirectly, via protein-protein interactions with other transcription factors (see, for example, Jonat et al., in *Cell* 62:1189–1204 (1990), Schuele et al., in *Cell* 62:1217–1226 (1990), and Yang-Yen et al., in *Cell* 62:1205–1215 (1990)). The steroid/thyroid receptor superfamily includes receptors for a variety of hydrophobic ligands including cortisol, aldosterone, estrogen, progesterone, testosterone, vitamin $D_3$, thyroid hormone and retinoic acid, as well as a number of receptor-like molecules, termed "orphan receptors" for which the ligands remain unknown (see Evans, 1988, supra). These receptors all share a common structure indicative of divergence from an ancestral archetype.

Identification of ligands for orphan receptors presents a significant challenge for the future since the number of orphan receptors which have been identified far exceeds the number of receptors with known ligands. Indeed, at least 40 genes, both vertebrate and invertebrate, have been identified which are structurally related to the steroid/thyroid receptor superfamily, but whose ligands are unidentified. Among these are Drosophila genes of known developmental significance including: the gap gene, knirps (Nauber et al., in *Nature* 336:489–492 (1988), the terminal gene tailless, involved in patterning the head and tail regions (Pignoni et al., in *Cell* 62:151–163 (1990), seven-up, which influences photoreceptor cell-fate (Mlodzik et al., in *Cell* 60: 211–224 (1990), and ultraspiracle, a gene required both maternally and zygotically for pattern formation (Oro et al., in *Nature* 347: 298–301 (1990)).

The identification of important Drosophila developmental genes as members of the steroid/thyroid hormone receptor superfamily suggests that vertebrate orphan receptors will have important developmental functions. Furthermore, the identification of ligands for orphan receptors could lead to the discovery of novel morphogens, teratogens and physiologically important hormones.

BRIEF DESCRIPTION OF THE INVENTION

In accordance with the present invention, we have identified new members of the steroid receptor superfamily of receptors, a representative member of which has been designated XOR-6. Invention receptors are responsive to hydroxy, mercapto or amino benzoates, and are expressed, for example, in *Xenopus laevis* embryos. XOR-6 is most closely, although distantly, related to the vitamin D3 receptor (VDR). The proteins are about 73% identical in amino acid sequence in the DNA-binding domains and about 42% identical in the ligand binding domain. Like VDR, XOR-6 has an extended D region between the DNA and ligand binding domains. Notably, the region amino-terminal to the XOR-6 DNA-binding domain is extremely acidic. This may influence its ability to activate target genes. XOR-6 is not restricted to Xenopus because southern blots show the presence of XOR-6-related sequences in a variety of other vertebrates. Indeed, a human genomic clone for an XOR-6 related gene has recently been isolated.

In accordance with a particular aspect of the present invention, there are also provided nucleic acid sequences encoding the above-identified receptors, as well as constructs and cells containing same, and probes derived therefrom. Furthermore, we have also discovered that hydroxy, mercapto or amino benzoates modulate the transcription activating effects of invention receptors.

BRIEF DESCRIPTION OF THE FIGURES

FIG. 1 presents a schematic comparison between XOR-6 and the human vitamin D3 receptor. The two amino acid sequences were aligned using the program GAP (see Devereaux et al., in *Nucl. Acids Res.* 12:387–395 (1984)). Similarity between XOR-6 and hVDR is expressed as percent amino acid identity.

FIG. 2 demonstrates that XOR-6 and hRXRα interact in vivo. The plasmids indicated in the figure were co-transfected into CV-1 cells along with the reporter tk(galp)3-luc and CMX-βgal. Note the strong suppression of basal transcription when GAL-XOR6 was added (right panel). This is characteristic of previously characterized ligand-dependent RXR heterodimeric partners.

FIG. 3 illustrates the activation of XOR-6 by a variety of amino benzoate derivatives. Thus, $10^{-6}$M of each compound was tested in the co-transfection assay for its ability to activate GAL-XOR6. Comparable results were obtained with full-length XOR-6.

DETAILED DESCRIPTION OF THE INVENTION

In accordance with the present invention, we have identified new members of the steroid receptor superfamily of receptors, a representative member of which has been designated XOR-6. Invention receptors are responsive to hydroxy, mercapto or amino benzoates, and are expressed, for example, in *Xenopus laevis* embryos. Invention receptor comprises a protein of approximately 386 amino acids (see SEQ ID NO:2), which is most closely, although distantly, related to the vitamin D3 receptor (VDR). Also provided herein is a 2191 bp cDNA which encodes an example of invention receptors (see SEQ ID NO:1).

XOR-6 and VDR are about 73% identical in amino acid sequence in the DNA-binding domains and about 42% identical in the ligand binding domain. Like the VDR, XOR-6 has an extended D region between the DNA and ligand binding domains. Notably, the region amino-terminal to the XOR-6 DNA-binding domain is extremely acidic. This may influence its ability to activate target genes. XOR-6 is not restricted to Xenopus because southern blots show the presence of XOR-6-related sequences in a variety of other vertebrates.

XOR-6 was discovered as part of a search for nuclear receptors expressed early in *Xenopus laevis* development. Thus, cDNAs encoding transcripts from nine different genes were isolated. These included xRARα, xRARγ, xRXRα, xRXRγ and five different orphan receptors. The presence of this diversity of receptors early in development suggests that their ligands might play important roles in morphogenetic signalling processes. Therefore it was of particular interest to identify those orphan receptors which had a high probability of showing ligand dependence.

Because most known RXR heterodimeric partners are ligand responsive, the above-described orphan receptor collection was screened for the ability to heterodimerize with RXR both in vitro and in vivo. One such orphan receptor, XOR-6 (for Xenopus Orphan Receptor 6). XOR-6 is a novel heterodimeric partner for RXR both in vitro and in vivo, further extending the family of nuclear receptors which require RXR for high-efficiency DNA-binding. XOR-6:RXR heterodimers apparently prefer to bind direct repeats separated by four nucleotides (DR-4), as does the thyroid hormone receptor. XOR-6 expression significantly blunts the ability of RAR to activate gene expression suggesting that these two signalling pathways block each other's ability to activate gene expression perhaps by influencing their common heterodimeric partner, RXR.

Based on the presumption that XOR-6 and its ligand must be co-expressed at some time during development, an unbiased, bioassay directed screen for XOR-6 agonists in HPLC fractionated organic extracts derived from a mixture of developmental stages was undertaken. A potent agonist was purified, and identified as 3-amino-ethyl-benzoate (3-AEB). Specific binding of 3-AEB to XOR-6 has been demonstrated herein, identifying it as a true ligand for this receptor. Additional ligands for XOR-6, e.g., hydroxy benzoates and mercapto benzoates, have also been identified. Accordingly, XOR-6 and ligands therefor represent a hitherto unknown hormonal signalling pathway.

RNAse protection assays were employed to measure steady-state mRNA levels over a developmental time sequence. XOR-6 mRNA is present in the unfertilized egg and remains at a relatively constant level until after gastrulation. It persists thereafter at a much reduced level until at least stage 45. To investigate whether XOR-6 mRNA is localized in the pre-midblastula embryo, blastulae were dissected into three major components, the animal cap, marginal zone and endoderm. RNAse protection analysis showed that there is no obvious localization of the maternally encoded XOR-6 mRNA at this stage.

Zygotic transcripts first become noticeable during neurulation (stage 14) where they appear in the anterior neural folds and the region lateral thereto. As the neural folds close, staining becomes more medial until finally appearing as an inverted Y at about stage 20. This is exactly the same pattern as cells which give rise to the hatching gland. Interestingly, this staining pattern defines boundaries of the future head. By stage 38, XOR-6 mRNA is restricted to the head, but is not limited to the hatching gland.

In vitro DNA-binding studies were used to determine the DNA-binding specificity of XOR-6. XOR-6 and hRXRα are seen to heterodimerize and bind DNA in a cocktail of response elements. This binding is strongly cooperative, as neither receptor alone showed DNA-binding at the protein concentrations used in the assay. This binding is also specific to hRXRα, because hRARα does not enhance XOR-6 DNA binding. Similar results are obtained using xRXRα.

A finer analysis of XOR-6:hRXRα binding specificity shows that the heterodimer binds to a subset of the known response elements in the cocktail: it binds weakly to DR-3 (but not the osteopontin vitamin D response element (SPP-VDRE), which is a variant of DR-3), strongly to DR-4 (and the murine leukemia virus (MLV-TRE), a DR-4-like element), and weakly to DR-5 (but strongly to the RARβ response element, a DR-5-like element). No significant binding is seen to synthetic or natural response elements corresponding to DR-0,1,2 or 6 (i.e., direct repeats having spacers of 0, 1, 2 or 6 nucleotides, respectively). These data indicate that the XOR-6:hRXRα heterodimer prefers to bind a DNA sequence consisting of directly-repeated AGTTCA half sites, separated by four nucleotides.

It was next tested to determine whether the XOR6:xRXRα heterodimer exhibited the predicted DNA-binding specificity. In vitro transcribed, translated XOR-6 and xRXRα proteins were tested for binding to direct repeats of AGTTCA separated by 1, 2, 3, 4, or 5 nucleotides (see Perlmann et al., in *Genes Dev.* 7:1411–1422 (1993)). The heterodimer is observed to exhibit the expected binding specificity to a response element comprising two half-sites (each having the sequence AGTTCA) separated by 4 nucleotides. This allowed the design of a specific XOR-6 reporter gene, tk-X6RE-luc (wherein the response element has the sequence AGTTCA TGAG AGTTCA; SEQ ID NO:3), which can be activated by XOR-6 in the presence of HPLC-purified embryo extracts.

In order to demonstrate that XOR-6 and RXR interact in vivo, a modification of the two hybrid system (see Fields and Song, in *Nature* 340:245–246 (1989), or Nagpal et al., in *Cell* 70:1007–1019 (1992)) was employed. This system relies on functional dimeric interactions between two proteins, one carrying the ability to bind a particular DNA-response element, and the other carrying the transactivation function, to reconstitute DNA-binding and transcriptional activation in a single complex.

Figure 1:
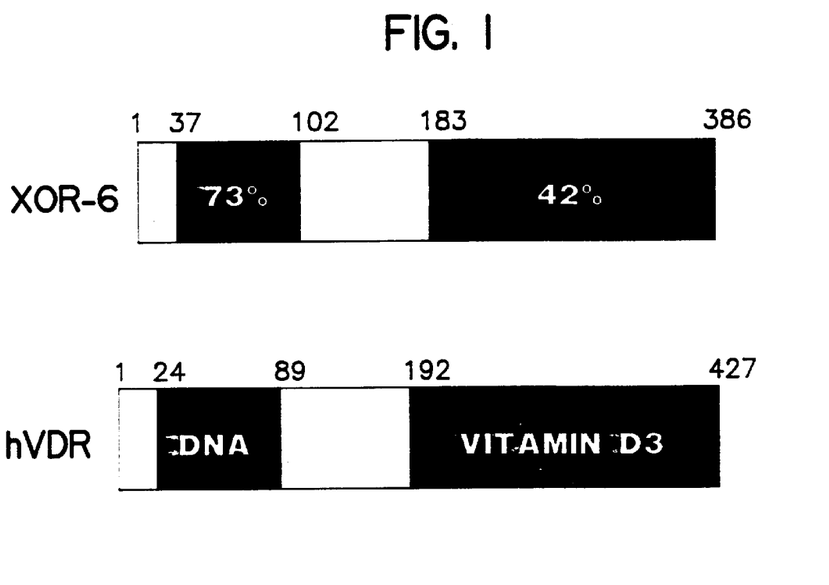
Figure 2:
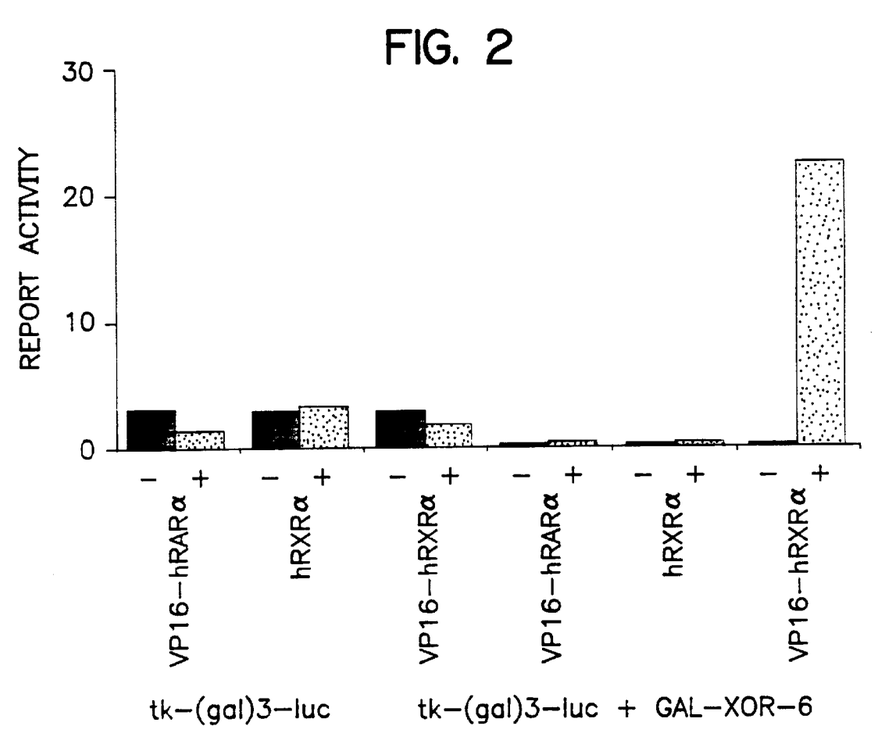

Applying this system to XOR-6 and RXR, VP16-hRXRα (a constitutive activator), GAL-XOR-6 and tk(gal$_p$)$_3$-luc were employed. Functional interaction between XOR-6 and hRXRα should lead to constitutive activation of the reporter gene when all three constructs are transfected together. VP16-hRXRα alone does not activate the reporter because it lacks the ability to bind to a GAL4 response element. Activation of the reporter occurs only when GAL-XOR-6 and VP16-hRXRα are cotransfected. Moreover, GAL-XOR-6 shows strong suppression of reporter gene basal activity (gee FIG. 2), which parallels effects elicited by GAL-hRARα, GAL-hTRβ and GAL-hVDR. Based on these observations, it can be concluded that XOR-6 and hRXRα can form functional heterodimers in vivo, that GAL-XOR-6 is unable to activate target genes in the absence of its ligand, and that unliganded GAL-XOR6, like most other ligand-dependent RXR partners, suppresses basal activity of a reporter construct to which it can bind.

To demonstrate that XOR-6 hormone responsiveness differs from that of other RXR dimeric partners (e.g., RAR, VDR, TR, and PPAR), the response of GAL-XOR-6 to agonists for the above receptors was tested. GAL-XOR-6 was not activated by a cocktail containing thyroid hormone ($10^{-7}$M), vitamin D3 ($10^{-7}$M), all-trans RA ($10^{-6}$M), or the peroxisome proliferator WY-14,643 ($5 \times 10^{-6}$M), while GAL-VDR, GAL-hRARα, GAL-hTRβ, and GAL-mPPARα are activated by the cocktail. It can be concluded, therefore, that XOR-6 defines a novel RXR-dependent, ligand-mediated signalling pathway.

A search for the XOR-6 ligand was instituted based on the presumption that the receptor and its ligand must be co-expressed at some time during development. Accordingly, an unbiased, bioassay directed screen for XOR-6 agonists was undertaken in HPLC fractionated organic extracts derived from a mixture of developmental stages. Total lipid extracts from a mixture of embryonic stages from fertilized eggs through swimming tadpoles were prepared and tested for the ability to activate both GAL-XOR6 or full-length XOR-6 in transfected CV-1 cells.

The total extract was partitioned between iso-octane and MeOH and again tested for bioactivity. Since the methanol phase contained most of the activity, it was further partitioned between ethyl acetate and $H_2O$. The ethyl acetate phase was shown to contain most of the activity and was thus further purified by reverse phase HPLC using several solvent systems. Absorbance was monitored between 200 and 600 nm, fractions were collected, dried and tested in the cotransfection assay (see, for example, U.S. Pat. No. 5,071,773) for their ability to activate full-length and GAL-XOR6. The eluted, purified agonist was subjected to high resolution mass spectroscopy which yielded a mass/charge ratio of 165.19 daltons. This predicted a molecular formula of $C_9H_{11}O_2N$, which most closely matches the ethyl ester of amino benzoic acid (AEB). The fragmentation pattern in Electron Impact mass spectroscopy suggests the meta isomer of AEB as the predominant form.

The ortho, meta and para amino ethyl benzoates were tested for agonist activity in the cotransfection assay. All three activated XOR-6 with a rank order potency as follows:

3-AEB>4-AEB>>2-AEB.

3-AEB co-chromatographed with purified agonist and gave an identical UV spectrum to authentic 3-AEB. Thus, 3-AEB is unequivocally identified as the purified agonist. Moreover, 3-AEB specifically activates XOR-6 alone among an extensive collection of published and unpublished vertebrate nuclear receptors.

In order to investigate ligand binding, the protease protection assay described by Leng et al., in *J. Ster. Bioch. and Mol. Biol.* 46:643–661 (1993) and Keidel et al, in *Mol. Cell. Biol.* 14:287–298 (1994) was utilized. Thus, $^{35}$S-labelled in vitro transcribed translated protein was incubated with increasing concentrations of various proteases in the presence of solvent carrier or the putative ligand. The presence of 3-AEB results in some protection from trypsin cleavage with a concomitant increase in the intensity of the intermediately sized cleavage products. This result is not seen in parallel experiments with xRARα or xRXRα, again suggesting specificity in ligand binding.

Figure 3:
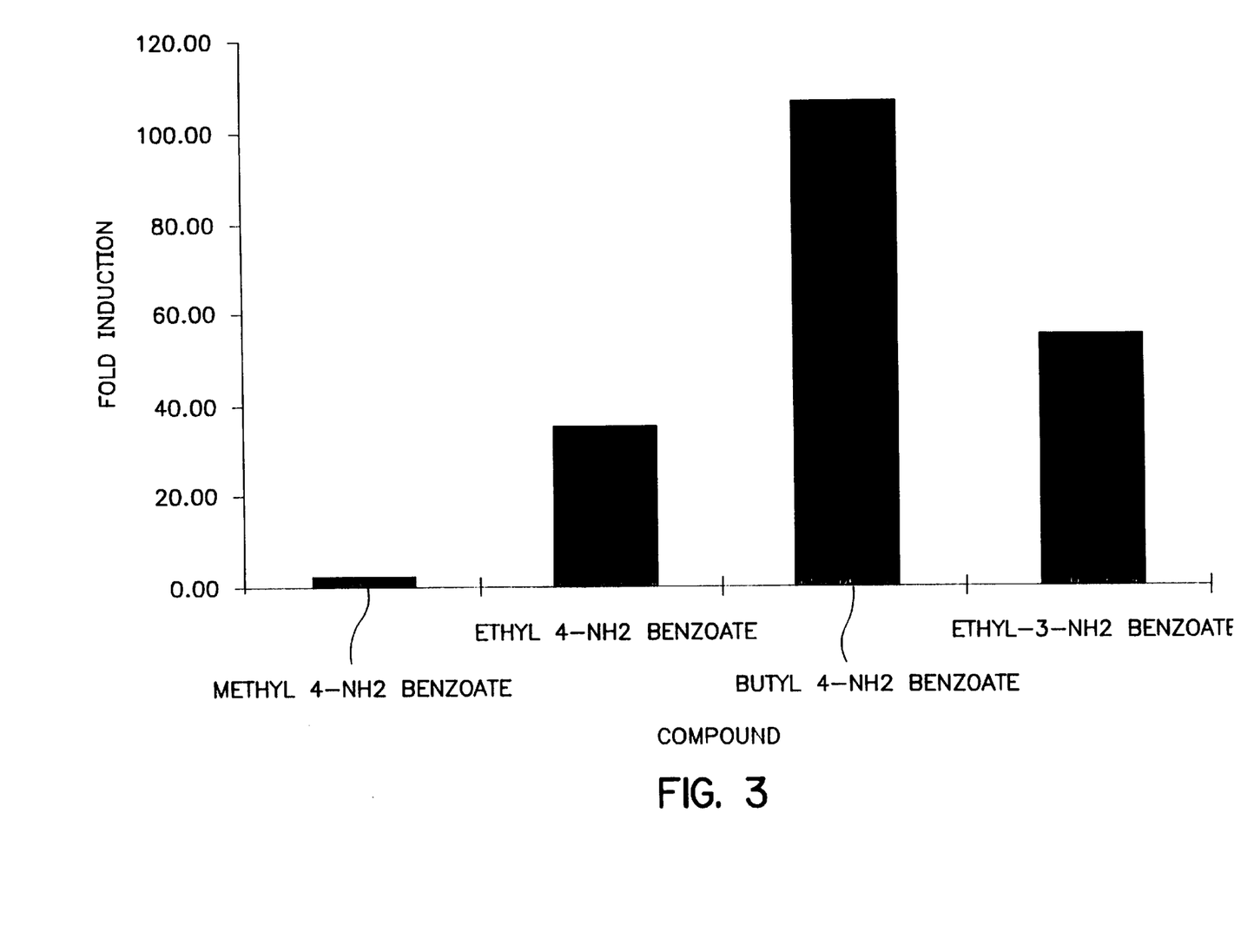

It was next attempted to determine whether compounds related to 3-AEB might also function as ligand for invention receptor. One likely candidate is the vitamin, 4-amino-benzoic acid (PABA). It was not possible, however, to demonstrate XOR-6 activation by 2-, 3-, or 4-amino benzoic acids, or the related 2-, 3-, or 4-amino salicylic acids. It is possible that the cell membrane is much less permeable to the acids than to the more lipophilic esters. This possibility was tested by comparing the activation by a series of esters differing in the length of the alkyl group. As shown in FIG. 3, the more lipophilic esters showed increased activation with a rank order potency of 4-amino-butyl benzoate>3-amino-ethyl benzoate>4-amino-ethyl benzoate>>4-amino methyl benzoate. These results suggest that the limiting step in XOR-6 activation is the transport of the ligand through the cell membrane. In conjunction with these studies, additional substituted benzoates, e.g., hydroxy benzoates and mercapto benzoates, have also been identified as ligands for invention receptor.

Figure 4:
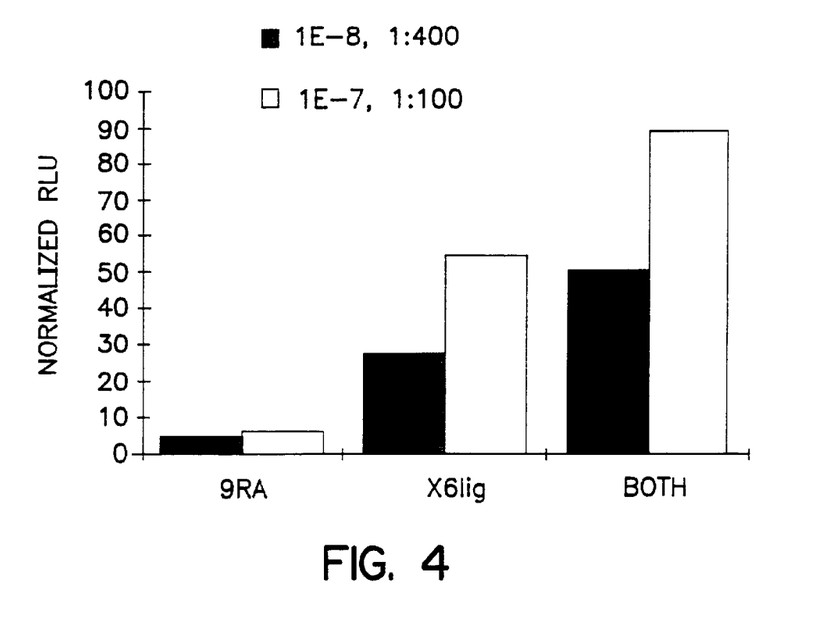
FIG. 4 illustrates the interaction of XOR-6 and RA signalling pathways, specifically demonstrating the synergism between partially purified XOR-6 agonist and the RXR ligand 9-cis RA. Receptors were transfected into cells and incubated with the indicated concentrations of agonists.

A potentially significant property of the XOR6:xRXRα heterodimer is its responsiveness to two ligands. Thus, in co-transfection experiments, either 9-cis RA or the partially purified agonist stimulated reporter gene expression in a receptor dependent manner. Unlike the response of RAR, VDR and TR heterodimers with RXR, which show additive effects on transcription, the XOR-6 ligand synergizes with 9-cis retinoic acid to activate its reporter gene (see FIG. 4), reminiscent of the situation with PPAR (see Kliewer et al., in *Nature* 358:771–774 (1992)). This synergism occurs at several dilutions of the XOR-6 agonist and concentrations of 9-cis RA (see FIG. 4). The demonstration of another heterodimer with dual hormone-responsiveness suggests that nuclear receptor heterodimers can generate combinatorial diversity by creating complexes with both novel DNA-binding properties and multiple hormonal activation levels. Such complexes would be ideal candidates for responding to combinations of graded morphogenetic signals during development.

Figure 5:
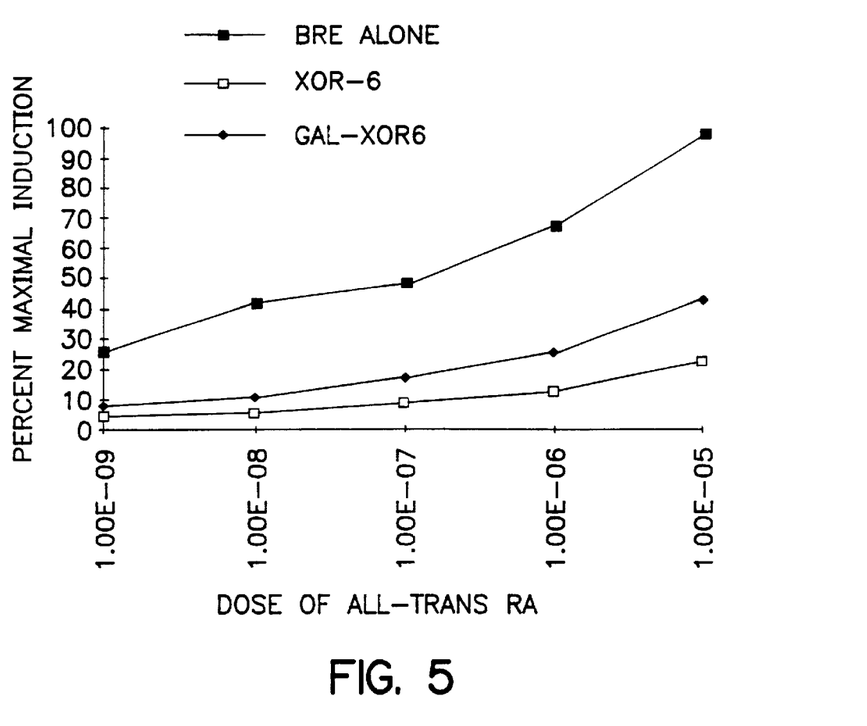
FIG. 5 illustrates the interaction of XOR-6 and RA signalling pathways, specifically demonstrating how the overexpression of full-length XOR-6, or the GAL-XOR-6 construct, interferes with retinoic acid (RA) signalling through the RARβ-RARE. 1 μg of XOR-6 expression plasmid was co-transfected into CV-1 cells with 5 μg of tk-β REx2-luc, and challenged with the indicated concentrations of all-trans retinoic acid.

Because XOR-6:RXR heterodimers bind well to a retinoic acid response element, βRARE, it was tested whether over-expression of XOR-6 could influence retinoic acid signalling through this element. As shown in FIG. 5, it is found that co-expression of XOR-6 and βRARE significantly blunts the retinoic acid-responsiveness of this promoter in a dose-dependent manner. This effect was strongest with full-length XOR-6 (24% of wild-type activity) but still detectable with GAL-XOR-6 (44% of wild-type activity). This suggests that maximal repression results from binding of XOR-6:RXR heterodimers to the βRARE, producing a non-productive transcription complex. The weaker inhibition by GAL-XOR-6 (which cannot bind to βRARE) suggests that sequestration of RXR in heterodimers unresponsive to retinoic acid also plays an inhibitory role.

In accordance with another embodiment of the present invention, there are provided a class of hydroxy, mercapto or amino benzoate compounds which are capable of acting as ligands for invention receptors. As employed herein, the phrase "hydroxy, mercapto or amino benzoate(s)" embraces compounds having the structure:

wherein
X is an hydroxy, alkoxy (of a lower alkyl, i.e., having 1–4 carbon atoms), mercapto, thioalkyl (of a lower alkyl), amino, alkylamino or acylamino group at the 2-, 3-, or 4-position of the ring,
each Y, when present, is independently selected from hydroxy, alkoxy, mercapto, thioalkyl, halide, trifluoromethyl, cyano, nitro, amino, carboxyl, carbamate, sulfonyl, sulfonamide, and the like, Z is selected from —OR' or —NHR', wherein R' is selected from hydrogen, $C_1$–$C_{12}$ alkyl, or $C_5$–$C_{10}$ aryl, and n is 0–2.

Presently preferred compounds embraced by the above generic formula include those wherein X is 2-, 3-, or 4-hydroxy or 3- or 4-amino, Z is alkoxy (i.e., methoxy, ethoxy or butoxy) and n is 0.

In accordance with yet another embodiment of the present invention, there are provided nucleic acids which encode the above-described receptor polypeptides. Exemplary DNAs include those which encode substantially the same amino acid sequence as shown in SEQ ID NO:2 (e.g., a contiguous nucleotide sequence which is substantially the same as nucleotides 166–1324 shown in SEQ ID NO:1). Preferred DNAs include those which encode the same amino acid sequence as shown in SEQ ID NO:2 (e.g., a contiguous nucleotide sequence which is the same as nucleotides 166–1324 shown in SEQ ID NO:1).

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

In accordance with still another embodiment of the present invention, there are provided DNA constructs comprising the above-described DNA, operatively linked to regulatory element(s) operative for transcription of said DNA and expression of said polypeptide in an animal cell in culture. There are also provided cells containing such construct, optionally containing a reporter vector comprising:

(a) a promoter that is operable in said cell, (b) a hormone response element, and (c) DNA encoding a reporter protein, wherein said reporter protein-encoding DNA is operatively linked to said promoter for transcription of said DNA, and wherein said promoter is operatively linked to said hormone response element for activation thereof.

In accordance with a still further embodiment of the present invention, there are provided probes comprising labeled single-stranded nucleic acid, comprising at least 20 contiguous bases in length having substantially the same sequence as any 20 or more contiguous bases selected from bases 1–2150, inclusive, of the DNA illustrated in SEQ ID NO:1, or the complement thereof. An especially preferred probe of the invention comprises at least 20 contiguous bases in length having substantially the same sequence as any 20 or more contiguous bases selected from bases 473–1324, inclusive, of the DNA illustrated in SEQ ID NO:1, or the complement thereof.

Those of skill in the art recognize that probes as described herein can be labelled with a variety of labels, such as for example, radioactive labels, enzymatically active labels, fluorescent labels, and the like. A presently preferred means to label such probes is with $^{32}P$. Such probes are useful, for example, for the identification of receptor polypeptide(s) characterized by being responsive to the presence of hydroxy, mercapto or amino benzoate(s) to regulate the transcription of associated gene(s), said method comprising hybridizing test DNA with a probe as described herein under high stringency conditions (e.g., contacting probe and test DNA at 65° C. in 0.5 M $NaPO_4$, pH 7.3, 7% sodium dodecyl sulfate (SDS) and 5% dextran sulfate for 12–24 hours; washing is then carried out at 60° C. in 0.1×SSC, 0.1% SDS for three thirty minute periods, utilizing fresh buffer at the beginning of each wash), and thereafter selecting those sequences which hybridize to said probe.

In another aspect of the invention, the above-described probes can be used to assess the tissue sensitivity of an individual to hydroxy, mercapto or amino benzoates by determining XOR-6 mRNA levels in a given tissue sample. It is expected that an individual having a high level of XOR-6 mRNA (or protein) will be sensitive to the presence of significant levels of amino benzoates, such as are used in sunscreen applications.

In accordance with yet another embodiment of the present invention, there are provided antibodies which specifically bind the above-described receptor polypeptides. Preferably, such antibodies will be monoclonal antibodies. Those of skill in the art can readily prepare such antibodies having access to the sequence information provided herein regarding invention receptors.

Thus, the above-described antibodies can be prepared employing standard techniques, as are well known to those of skill in the art, using the invention receptor proteins or portions thereof as antigens for antibody production. Both anti-peptide and anti-fusion protein antibodies can be used (see, for example, Bahouth et al. *Trends Pharmacol Sci.* 12:338–343 (1991); *Current Protocols in Molecular Biology* (Ausubel et al., eds.) John Wiley and Sons, New York (1989)). Factors to consider in selecting portions of the invention receptors for use as immunogen (as either a synthetic peptide or a recombinantly produced bacterial fusion protein) include antigenicity, uniqueness to the particular subtype, and the like.

The availability of such antibodies makes possible the application of the technique of immunohistochemistry to monitor the distribution and expression density of invention receptors. Such antibodies could also be employed for diagnostic and therapeutic applications.

In accordance with yet another embodiment of the present invention, there is provided a method of testing a compound for its ability to regulate transcriptionactivating effects of invention receptor polypeptide(s), said method comprising assaying for the presence or absence of reporter protein upon contacting of cells containing said receptor polypeptide and reporter vector with said compound;

wherein said reporter vector comprises:

(a) a promoter that is operable in said cell, (b) a hormone response element, and (c) DNA encoding a reporter protein, wherein said reporter protein-encoding DNA is operatively linked to said promoter for transcription of said DNA, and wherein said promoter is operatively linked to said hormone response element for activation thereof.

Hormone response elements suitable for use in the above-described assay method comprise two half sites (each having the sequence AGTTCA), separated by a spacer of 3, 4 or 5 nucleotides. Those of skill in the art recognize that any combination of 3, 4 or 5 nucleotides can be used as the spacer. Response elements having a spacer of 4 nucleotides (e.g., SEQ ID NO:3) are presently preferred.

Optionally, the above-described method of testing can be carried out in the further presence of ligand for invention receptors (e.g., a hydroxy, mercapto or amino benzoate), thereby allowing the identification of antagonists of invention receptors. Those of skill in the art can readily carry out antagonist screens using methods well known in the art. Typically, antagonist screens are carried out using a constant amount of agonist, and increasing amounts of a putative antagonist.

In accordance with a still further embodiment of the present invention, there is provided a method for modulating process(es) mediated by invention receptor polypeptides, said method comprising conducting said process(es) in the presence of at least one hydroxy, mercapto or amino benzoate (as defined hereinabove).

As shown herein, XOR-6 and RXR functionally interact both in vitro to preferentially bind a DR-4 type response element, and in vivo to activate a GAL4-based reporter in the two-hybrid assay. Thus a functional interaction has been identified between RXR and an orphan receptor within the cell to activate a reporter gene. This observation can be exploited to develop a high-sensitivity assay system for the XOR-6 ligand and for orphan receptor ligands in general, at least for those which interact with RXR.

The invention will now be described in greater detail by reference to the following non-limiting examples.

EXAMPLE 1 cDNA Isolation and Characterization

XOR-6 was identified in a screen for maternally-expressed nuclear hormone receptors (Blumberg et al., in *Proc. Natl. Acad. Sci. USA* 89:2321–2325 (1992). Three clones were identified from an egg cDNA library, an additional two were isolated from a dorsal blastopore lip cDNA library. The longest clone was sequenced completely on both strands using a combination of directed subcloning and specific oligonucleotide priming. DNA sequences were compiled and aligned using the programs of Staden (Staden, in *Nucleic Acids Res.* 14:217–231 (1986), University of Wisconsin Genetics Computer Group (Devereaux et al., 1984, *supra*, and Feng and Doolittle (Feng and Doolittle, in *J. Mol. Evol.* 215:351–260 (1987). Database searching was performed using the BLAST network server at the National Center for Biotechnology Information (Altschul et al., *J. Mol. Biol.* 215:403–410 (1990)).

EXAMPLE 2

RNA Preparation and Analysis

RNA was prepared from fertilized *Xenopus laevis* eggs and staged embryos as described by Blumberg et al., 1992, supra. The temporal and spatial patterns of expression were determined using RNAse protection as described by Blumberg et al., 1992, supra. The RNAse protection probes used are the following: EF-1α, nucleotides 790–1167; XOR-6, nucleotides 1314 to 1560, which represents the last three amino acids of the protein and part of the 3' untranslated region.

RNAse protection was performed with total RNA from the total ovary (10 μg); unfertilized egg (40 μg); 2-cell (40 μg); blastula (40 μg); gastrula (st 10, 10 μg), st 11, 8 μg); neurula (4 μg); tailbud (4 μg); swimming tadpole (4 μg). Alternatively, RNAse protection was performed with 20 μg of total RNA from whole embryos or dissected animal caps, marginal zone, and vegetal pole.

A lateral view of a stage 12 embryo hybridized with antisense XOR-6 reveals that hybridization extends from the anterior-most end of the involuting mesoderm to the dorsal blastopore lip.

For localization studies, stage 8–9 embryos were dissected into animal, marginal and vegetal fragments and RNA was prepared using a proteinase K method as described by Cho et al., in *Cell* 65:55–64 (1991). Whole-mount in situ hybridization was performed as described by Harland, (1991). The entire cDNA shown in SEQ ID NO:1 was used as a probe for in situ hybridization. To make anti-sense RNA, the Bluescript II SK-plasmid containing the cDNA was linearized with SmaI and transcribed with T7 RNA polymerase. To produce sense RNA, the plasmid was digested with EcoRV and transcribed with T3 RNA polymerase.

EXAMPLE 3

In vitro DNA-binding

DNA-binding analysis was performed using in vitro transcribed, translated proteins (Perlmann et al., 1993, supra. oligonucleotides employed have been described previously (see Umesono et al., in *Cell* 65:1255–1266 (1990) and Perlmann et al., 1993, supra).

Thus, in vitro transcribed and translated proteins were mixed with a cocktail of hormone response elements containing DR0, DR1, PPRE, DR2, MLV-TRE, SPP1, and β-RARE. Thus, XOR-6 and hRXRα proteins were mixed and incubated with radiolabelled response elements. DR-1 through 5 are direct repeats of the sequence AGTTCA separated by 1–5 nucleotides. Reaction conditions and gel electrophoresis employed were as described by Perlmann et al., 1993, supra.

EXAMPLE 4

Cell Culture and Transfection Studies

A suitable eukaryotic expression vector for use herein was constructed from the commercially available vector pCDNAI-AMP (Invitrogen). This vector allows expression from the strong cytomegalovirus early promoter, and bacteriophage T7 and SP6 promoter-driven production of sense and antisense RNA, respectively.

The cloning strategy employed was as follows: the three endogenous NcoI sites were removed by site directed mutagenesis, the polylinker region between XhoI and XbaI was removed by double digestion, endfilling and self ligation. A cassette consisting of the Xenopus β-globin leader and trailer derived from the plasmid pSP36T (see Amaya et al., in *Cell* 66:257–270 (1991)), separated by a synthetic polylinker (containing unique sites for NcoI, SphI, EcoRI, SalI, EcoRV, BamHI, and XbaI) was inserted between HindIII and NotI sites in the vector. The resulting plasmid, designated pCDG1, can be linearized with NotI to produce mRNA from the bacteriophage T7 promoter. The XOR-6 protein coding region was cloned between the NcoI and BamHI sites of pCDG1 and designated pCDG-XOR6.

pCMX-GAL4-XOR6 was constructed by cloning nucleotides encoding amino acids 103 to 386 of XOR-6 into the SalI to XbaI sites of pCMX-GAL4 (see U.S. Ser. No. 08/177,740).

pCMX-VP16 receptor chimeras were constructed by fusing the potent VP16 transactivation domain (see Sadowski et al., in *Nature* 335:563–564 (1988)) to the amino terminus of the full-length hRXRα (see Mangelsdorf et al., *Nature* 345:224–229 (1990)), hRARα (see Giguere et al., in *Nature* 330:624–629 (1987)), or VDR (see McDonnell et al., in *Mol. Endocrinol.* 3:635–644 (1989)) protein coding regions.

CV-1 cells were maintained in DMEM containing 10% resin-charcoal stripped fetal bovine serum. Liposomemediated transient transfections were performed using DOTAP reagent (Boehringer Manheim) at a concentration of 5 μg/ml in Opti-MEM (Gibco). After 12–18 hours, the cells were washed and fresh DMEM-10% serum was added, including receptor agonists if required. After a further 48 hour incubation, the cells were lysed and luciferase reporter gene assays and β-galactosidase transfection control assays performed. Reporter gene expression is normalized to the β-galactosidase transfection control and expressed as relative light units per O.D. per minute of β-galactosidase activity.

EXAMPLE 5

Organic Extraction and HPLC Analysis

Fresh or flash frozen embryos were homogenized in a large volume of 50% $CH_2Cl_2$/50% MeOH, typically 10 ml/gram of tissue. Denatured proteins were removed by filtration through diatomaceous earth and the liquid phase recovered and evaporated to dryness with a Buchi rotary evaporator. The resulting material was resuspended in a minimum volume of iso-octane and transferred to a separatory funnel. Non-polar and polar compounds were separated by partitioning between large volumes of iso-octane and MeOH. An agonist of XOR-6 partitioned primarily into the methanol layer.

The methanol phase was then dried, weighed, and partitioned between ethyl acetate and $H_2O$. An agonist for XOR-6 partitioned greater than 95% into ethyl acetate. The ethyl acetate phase was then dried, weighed, and fractionated by reverse phase HPLC, using several solvent systems.

Initially, the ethyl acetate phase was separated by isocratic elution utilizing a 7.8×300 mm Novapack C18 column (Waters), developed at 4 ml/min with 56% acetonitrile, 16% methanol, 28% 2% aqueous acetic acid (see Heyman et al., in *Cell* 68:1–20 (1992)). Absorbance was monitored between 200 and 600 nm using a Waters 996 photodiode array detector. Fractions were collected, dried and tested in the cotransfection assay for their ability to activate GAL-XOR6. Active fractions were pooled and rechromatographed on the same column using a gradient of methanol, 10 mM ammonium acetate (pH 7.5) beginning at 30% methanol, run isocratically for 15 minutes, and then increasing linearly to 100% methanol over the next 45 minutes. Fractions were again tested for bioactivity and the active fractions pooled.

Final purification was accomplished using a dioxane/water gradient beginning at 20% dioxane and run isocratically for 15 minutes, then increasing linearly to 100% dioxane over the next 30 minutes.

EXAMPLE 6

Ligand Binding

In order to investigate ligand binding, a protease protection assay was utilized (see Leng et al., 1993, supra, and Keidel et al, 1994, supra). $^{35}$S-labelled protein was produced by coupled in vitro transcription/translation (TNT, Promega) and incubated with increasing concentrations of trypsin, chymotrypsin or alkaline protease in the presence of solvent carrier or with $10^{-5}$M 3-amino ethylbenzoate (3-AEB) for 15 minutes at room temperature. The reactions were stopped with SDS-loading buffer and SDS-PAGE was performed on 12.5% acrylamide gels. Alterations in the size of protected fragments produced by added ligand in a dose dependent fashion was taken as evidence for specific binding.

3-AEB is seen to protect XOR-6 from trypsin digestion, thus confirming that 3-AEB binds XOR-6.

While the invention has been described in detail with reference to certain preferred embodiments thereof, it will be understood that modifications and variations are within the spirit and scope of that which is described and claimed.

That which is claimed is:

1. A method for modulating transcription activating effects mediated by nuclear receptor polypeptides wherein said receptor has substantially the same amino acid sequence as SEQ ID NO:2, or is encoded by a nucleic acid that hybridizes to a nucleic acid of SEQ ID NO:1 under high stringency conditions, said method comprising conducting said transcription in the presence of one or more of said receptor polypeptides and a compound having the structure:

wherein
X is a hydroxy, alkoxy, mercapto, thioalkyl, amino, alkylamino or acylamino group at the 2-3-, or 4-position of the ring,
each Y, when present, is independently selected from hydroxy, alkoxy, mercapto, thioalkyl, halide, trifluoromethyl, cyano, nitro, amino, carboxyl, carbamate, sulfonyl, or sulfonamide,
Z is selected from —OR' or —NHR', wherein R' is selected from hydrogen, $C_1$–$C_{12}$ alkyl or $C_5$–$C_{10}$ aryl, and
n is 0–2.

2. A method according to claim 1, wherein said compound is at least one hydroxy, mercapto or amino benzoate.

3. A method according to claim 1 wherein X is 3- or 4-amino, Z is alkoxy and n is 0.

4. A method according to claim 3 wherein Z is selected from methoxy, ethoxy or butoxy.

5. A method according to claim 1 wherein X is 2-, 3- or 4-hydroxy, Z is alkoxy and n is 0.

6. A method according to claim 5 wherein Z is selected from methoxy, ethoxy or butoxy.

7. A method of testing a compound for its ability to regulate transcription-activating effects of a nuclear receptor polypeptide wherein said receptor has substantially the same amino acid sequence as SEQ ID NO:2, or is encoded by a nucleic acid that hybridizes to a nucleic acid of SEQ ID NO:1 under high stringency conditions, said method comprising assaying for a change in expression of reporter protein upon contacting of test cells with said compound, as compared to the expression of said reporter protein in the absence of said compound, and identifying as a compound that regulates the transcription-activating effects of said receptor those which cause a change in expression of said reporter protein when compared to the expression of said reporter in the absence of said compound;
wherein said test cell comprises said receptor polypeptide and reporter vector,
wherein said reporter vector comprises:
(a) a promoter that is operable in said test cell,
(b) a hormone response element for said receptor, and
(c) DNA encoding said reporter protein,
wherein said reporter protein-encoding DNA is operatively linked to said promoter for transcription of said DNA,
wherein said promoter is operatively linked to said hormone response element for activation thereof by said receptor polypeptide.

8. A method according to claim 7, wherein said receptor has substantially the same amino acid sequence as SEQ ID NO:2.

9. A method according to claim 7, wherein said cells also express RXR.

10. A method according to claim 7, comprising conducting said transcription in the presence of RXR.

11. A method according to claim 7, wherein said receptor is further characterized as being responsive to the presence of hydroxy, mercapto or amino benzoate(s) to regulate the transcription of associated gene(s), said hydroxy, mercapto or amino benzoate(s) are compounds having the structure:

wherein:
N is an amino, hydroxy or mercapto-substituted aryl moiety, and
Z is —OR' or —NHR', wherein R' is hydrogen, $C_1$–$C_{12}$ alkyl or $C_5$–$C_{10}$ aryl.

12. A method according to claim 11, wherein said contacting is carried out in the further presence of at least one of said hydroxy, mercapto or amino benzoate(s).

13. A method of testing a compound for its ability to regulate transcription-activating effects of a nuclear receptor polypeptide wherein said receptor is encoded by a nucleic acid that has substantially the same sequence as the nucleic acid of SEQ ID NO:1, said method comprising assaying for a change in expression of reporter protein upon contacting of test cells with said compound, as compared to the expression of said reporter protein in the absence of said compound, and identifying as a compound that regulates the transcription-activating effects of said receptor those which cause a change in expression of said reporter protein when compared to the expression of said reporter in the absence of said compound;
wherein said test cell comprises said receptor polypeptide and reporter vector,
wherein said reporter vector comprises:
(a) a promoter that is operable in said test cell,
(b) a hormone response element for said receptor, and
(c) DNA encoding said reporter protein,
wherein said reporter protein-encoding DNA is operatively linked to said promoter for transcription of said DNA,
wherein said promoter is operatively linked to said hormone response element for activation thereof by said receptor polypeptide.

14. A method of testing a compound for its ability to regulate transcription-activating effects of a nuclear receptor polypeptide wherein said receptor comprises a DNA binding domain having at least about 73 percent homology with residues 37–102 of the amino acid sequence of SEQ ID NO:2, said method comprising assaying for a change in expression of reporter protein upon contacting of test cells with said compound, as compared to the expression of said reporter protein in the absence of said compound, and identifying as a compound that regulates the transcription-activating effects of said receptor those which cause a change in expression of said reporter protein when compared to the expression of said reporter in the absence of said compound;

wherein said test cell comprises said receptor polypeptide and reporter vector, wherein said reporter vector comprises:
(a) a promoter that is operable in said test cell,
(b) a hormone response element for said receptor, and
(c) DNA encoding said reporter protein,
wherein said reporter protein-encoding DNA is operatively linked to said promoter for transcription of said DNA,
wherein said promoter is operatively linked to said hormone response element for activation thereof by said receptor polypeptide.

15. A method according to claim 14, wherein said receptor is further characterized by being responsive to the presence of hydroxy, mercapto or amino benzoate(s) and/or ester and/or imido derivatives thereof to regulate the transcription of associated gene(s).

16. A method according to claim 14, wherein said receptor further comprises: a ligand binding domain having at least about 42 percent homology to residues 183–386 of the amino acid sequence of SEQ ID NO:2.

17. A method according to claim 16, wherein said receptor is further characterized by being responsive to the presence of hydroxy, mercapto or amino benzoate(s) and/or ester and/or imido derivatives thereof to regulate the transcription of associated gene(s).

18. A method for modulating transcription activating effects mediated by nuclear receptor polypeptides wherein said receptor is encoded by a nucleic acid that has substantially the same sequence as the nucleic acid of SEQ ID NO:1, said method comprising conducting said transcription in the presence of one or more of said receptor polypeptides and a compound having the structure:

wherein
X is a hydroxy, alkoxy, mercapto, thioalkyl, amino, alkylamino or acylamino group at the 2-3-, or 4-position of the ring,
each Y, when present, is independently selected from hydroxy, alkoxy, mercapto, thioalkyl, halide, trifluoromethyl, cyano, nitro, amino, carboxyl, carbamate, sulfonyl, or sulfonamide,
Z is selected from —OR' or —NHR', wherein R' is selected from hydrogen, $C_1$–$C_{12}$ alkyl or $C_5$–$C_{10}$ aryl, and
n is 0–2.

19. A method for modulating transcription activating effects mediated by nuclear receptor polypeptides wherein said receptor comprises a DNA binding domain having at least about 73 percent homology with residues 37–102 of the amino acid sequence of SEQ ID NO:2, said method comprising conducting said transcription in the presence of one or more of said receptor polypeptides and a compound having the structure:

wherein
X is a hydroxy, alkoxy, mercapto, thioalkyl, amino, alkylamino or acylamino group at the 2-3-, or 4-position of the ring,
each Y, when present, is independently selected from hydroxy, alkoxy, mercapto, thioalkyl, halide, trifluoromethyl, cyano, nitro, amino, carboxyl, carbamate, sulfonyl, or sulfonamide,
Z is selected from —OR' or —NHR', wherein R' is selected from hydrogen, $C_1$–$C_{12}$ alkyl or $C_5$–$C_{10}$ aryl, and
n is 0–2.

20. A method according to claim 19, wherein said receptor is further characterized by being responsive to the presence of hydroxy, mercapto or amino benzoate(s) and/or ester and/or imido derivatives thereof to regulate the transcription of associated gene(s).

21. A method according to claim 19, wherein said receptor further comprises:
a ligand binding domain having at least about 42 percent homology to residues 183–386 of the amino acid sequence of SEQ ID NO:2.

22. A method according to claim 21, wherein said receptor is further characterized by being responsive to the presence of hydroxy, mercapto or amino benzoate(s) and/or ester and/or imido derivatives thereof to regulate the transcription of associated gene(s).

* * * * *

UNITED STATES PATENT AND TRADEMARK OFFICE
CERTIFICATE OF CORRECTION

PATENT NO.    : 6,391,847 B1
DATED         : May 21, 2002
INVENTOR(S)   : Evans et al.

It is certified that error appears in the above-identified patent and that said Letters Patent is hereby corrected as shown below:

<u>Column 1,</u>
Line 4, please insert the following acknowledgement:
-- ACKNOWLEDGMENT This invention was made with United States Government support under Grant Nos. HD-27283, HD-27700 and GM-26444 awarded by the National Institutes of Health. The Government has certain rights in the invention. --

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,391,847 B1  
DATED : May 21, 2002  
INVENTOR(S) : Ronald M. Evans, Bruce Blumberg and Kazuhiko Umesono It is certified that error appears in the above-identified patent and that said Letters Patent is hereby corrected as shown below:

<u>Title page, Item [54] and Column 1, lines 1-3,</u>
The title should read as follows:
-- METHOD EMPLOYING XOR-6, A VITAMIN D-LIKE RECEPTOR FROM XENOPUS --

Signed and Sealed this

Third Day of June, 2003

JAMES E. ROGAN
*Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2191 base pairs
      (B) TYPE: nucleic acid
      (C) STRANDEDNESS: both
      (D) TOPOLOGY: both    (ii) MOLECULE TYPE: cDNA    (ix) FEATURE:
      (A) NAME/KEY: CDS
      (B) LOCATION: 167..1324
      (D) OTHER INFORMATION: /product= "XOR-6 RECEPTOR"

(xi) SEQUENCE DESCRIPTION: SEQ ID NO:1:

```
TGAGAGTGAG AATCCCGGGC TCAGCCGCTC ACCTGTCCGG ATAGAGAGTT G GGATGTGAG      60

AGGGACAGAA GGGCGGGGCT AGTGCAGGTG TATCGGCCGC TCGAGGAGCT G CTCAGTGAA     120

AGAGAGAAGT GGCGAACGCT GGGACCAAGG TTTCTGTGAC AAAACG ATG TGG AAA         175
                                                Met Trp Lys
                                                 1
```

-continued

```
GTG CAG GAG ACT TTG GTA CTG GAG GAA GAA G AG GAG GAA GAA GAC GCC      223
Val Gln Glu Thr Leu Val Leu Glu Glu Glu G lu Glu Glu Glu Asp Ala
  5                  10                  15

TCT AAC AGT TGT GGG ACG GGG GAA GAC GAG G AC GAT GGG GAC CCC AAG      271
Ser Asn Ser Cys Gly Thr Gly Glu Asp Glu A sp Asp Gly Asp Pro Lys
 20                  25                  30                  35

ATC TGC CGT GCG TGT GGG GAC CGG GCC ACT G GG TAT CAC TTC AAT GCT      319
Ile Cys Arg Ala Cys Gly Asp Arg Ala Thr G ly Tyr His Phe Asn Ala
                 40                  45                  50

ATG ACC TGC GAG GGC TGC AAG GGA TTC TTC A GG CGG GCC GTG AAG AGG      367
Met Thr Cys Glu Gly Cys Lys Gly Phe Phe A rg Arg Ala Val Lys Arg
             55                  60                  65

AAC TTG CGG CTC AGC TGC CCC TTC CAG AAT T CC TGC GTC ATC AAC AAG      415
Asn Leu Arg Leu Ser Cys Pro Phe Gln Asn S er Cys Val Ile Asn Lys
         70                  75                  80

AGC AAT CGG CGC CAC TGC CAG GCC TGT CGG C TC AAG AAA TGT CTG GAC      463
Ser Asn Arg Arg His Cys Gln Ala Cys Arg L eu Lys Lys Cys Leu Asp
     85                  90                  95

ATC GGC ATG AGG AAA GAG TTG ATC ATG TCC G AT GCA GCG GTG GAA CAG      511
Ile Gly Met Arg Lys Glu Leu Ile Met Ser A sp Ala Ala Val Glu Gln
100                 105                 110                 115

AGA CGA GCG CTA ATT AAG AGA AAA CAC AAA T TA ACG AAA TTG CCC CCC      559
Arg Arg Ala Leu Ile Lys Arg Lys His Lys L eu Thr Lys Leu Pro Pro
                120                 125                 130

ACA CCC CCA GGG GCC AGT CTG ACT CCA GAG C AG CAG CAC TTT CTC ACT      607
Thr Pro Pro Gly Ala Ser Leu Thr Pro Glu G ln Gln His Phe Leu Thr
            135                 140                 145

CAA CTG GTT GGG GCC CAC ACC AAA ACC TTT G AC TTC AAC TTC ACC TTC      655
Gln Leu Val Gly Ala His Thr Lys Thr Phe A sp Phe Asn Phe Thr Phe
        150                 155                 160

TCC AAG AAC TTT CGG CCA ATA AGA AGA TCT T CA GAC CCA ACT CAG GAG      703
Ser Lys Asn Phe Arg Pro Ile Arg Arg Ser S er Asp Pro Thr Gln Glu
    165                 170                 175

CCC CAA GCC ACC TCT TCT GAA GCC TTT TTG A TG CTA CCT CAT ATA TCT      751
Pro Gln Ala Thr Ser Ser Glu Ala Phe Leu M et Leu Pro His Ile Ser
180                 185                 190                 195

GAC CTC GTT ACC TAC ATG ATC AAG GGC ATC A TC AGC TTT GCC AAA ATG      799
Asp Leu Val Thr Tyr Met Ile Lys Gly Ile I le Ser Phe Ala Lys Met
                200                 205                 210

CTC CCC TAC TTC AAG AGT CTG GAC ATT GAA G AC CAA ATT GCT CTC CTG      847
Leu Pro Tyr Phe Lys Ser Leu Asp Ile Glu A sp Gln Ile Ala Leu Leu
            215                 220                 225

AAA GGT TCT GTA GCG GAG GTT TCT GTG ATC C GA TTC AAC ACT GTG TTT      895
Lys Gly Ser Val Ala Glu Val Ser Val Ile A rg Phe Asn Thr Val Phe
        230                 235                 240

AAC TCT GAC ACC AAT ACG TGG GAG TGT GGC C CC TTC ACC TAT GAC ACT      943
Asn Ser Asp Thr Asn Thr Trp Glu Cys Gly P ro Phe Thr Tyr Asp Thr
    245                 250                 255

GAG GAT ATG TTC CTG GCC GGC TTC CGT CAG C TG TTC CTG GAG CCC CTG      991
Glu Asp Met Phe Leu Ala Gly Phe Arg Gln L eu Phe Leu Glu Pro Leu
260                 265                 270                 275

GTG AGG ATT CAT CGC ATG ATG AGG AAA CTG A AT GTA CAG AGT GAG GAA     1039
Val Arg Ile His Arg Met Met Arg Lys Leu A sn Val Gln Ser Glu Glu
                280                 285                 290

TAC GCC ATG ATG GCC GCT CTG TCC ATT TTC G CT TCT TAC CGA CCG GGG     1087
Tyr Ala Met Met Ala Ala Leu Ser Ile Phe A la Ser Tyr Arg Pro Gly
            295                 300                 305

GTC TGC GAC TGG GAG AAG ATC CAG AAG CTG C AG GAA CAC ATT GCC CTG     1135
Val Cys Asp Trp Glu Lys Ile Gln Lys Leu G ln Glu His Ile Ala Leu
```

```
               310                 315                    320
ACA CTA AAA GAT TTC ATC GAC AGC CAA CGG C CC CCC TCC CCG CAG AAC     1183
Thr Leu Lys Asp Phe Ile Asp Ser Gln Arg P ro Pro Ser Pro Gln Asn
        325                 330                335

AGG CTC CTG TAC CCC AAG ATC ATG GAG TGT C TG ACA GAG CTT CGG ACA     1231
Arg Leu Leu Tyr Pro Lys Ile Met Glu Cys L eu Thr Glu Leu Arg Thr
340                 345                 350                 355

GTC AAT GAC ATA CAC AGC AAG CAG CTC CTG G AG ATC TGG GAC ATT CAG     1279
Val Asn Asp Ile His Ser Lys Gln Leu Leu G lu Ile Trp Asp Ile Gln
                360                 365                 370

CCT GAT GCC ACC CCA CTT ATG CGA GAA GTC T TT GGA TCC CCT GAA         1324
Pro Asp Ala Thr Pro Leu Met Arg Glu Val P he Gly Ser Pro Glu
            375                 380                 385

TGAGTGATGA GCACATTCCT ACTGTGAGAG TCGCTGACCC CACCGGGAAG C TTGGGCTCC   1384

TTCTACTGGC GTCTGTCCTG GTAGGGCAAT GTGGCCTTCA AAGCATCAGC A GCCGGTGGA   1444

TTGTCTTCTA CTGACACCAT CTTGTTCATT GCTCAGACGT TGCTTCAGTC C CATTGGGTC   1504

GAGGAGTTTA TGGAAAACTC TACCTTGTGG GATATCGGGG GGGGGAACAT G GAATTCCCA   1564

TCTGGGTCAC CAACATGTGA AGAAACTGG TTCTGAGGAG CCAAAATGTT C TGCTGGACA    1624

AAAAGGAATG AAGTCACATA GAGACGAGTG TGGTCCAATA AGAGACAGT C TGGCCAGAG    1684

ACAATGTGAC TGGTCCAATA TGAGTGGACA ATAAAGCAAC TCCCTGATCC T ACAACTGGT   1744

TCCTGCAGGT TCTGCGCTGG GTTTGTGGCT CATTTAGATC AGGAGTTTGG T ACCTGCACT   1804

AATTCTGTTC TTTTACGACT GACTCGGCTG AATGAAAGGG GCTGTCACTT G TAGCCGGCG   1864

ACGTGGGACA TTAGCCACAA GCCAAATCTT CTCAGGGAAG CCAAATGGGC T GGGGGTGT    1924

AACACTGGGG GCACCAGACA AACTGTAACT AAATGAGGTT TAATCTCAGG G CTCCTGTAA   1984

TTATACTGAC CCCCCACTTG GGATAGGGC TAAATATTGG GGGTCTGGGA G TTCTGTTCC    2044

AGAAGGTATT GGGGTGGGGG TCTATGGGTT GGGCCTGTGT TAGACGAGTG T TTGTAGCCG   2104

TTCCCTGTGT CTATTTAGTT CTGGTGTTTC TGGTACCGTA TTGGGCTCCA A ATTGTTTTA   2164

TTCATAAAAA AAAAAAAAAA ACTCGAG                                       2191

(2) INFORMATION FOR SEQ ID NO:2:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Lys Val Gln Glu Thr Leu Val Leu G lu Glu Glu Glu Glu
  1               5                  10                 15

Glu Asp Ala Ser Asn Ser Cys Gly Thr Gly G lu Asp Glu Asp Gly
             20                  25                  30

Asp Pro Lys Ile Cys Arg Ala Cys Gly Asp A rg Ala Thr Gly Tyr His
             35                  40                  45

Phe Asn Ala Met Thr Cys Glu Gly Cys Lys G ly Phe Phe Arg Arg Ala
         50                  55                  60

Val Lys Arg Asn Leu Arg Leu Ser Cys Pro P he Gln Asn Ser Cys Val
 65                  70                  75                  80

Ile Asn Lys Ser Asn Arg Arg His Cys Gln A la Cys Arg Leu Lys Lys
                 85                  90                  95

Cys Leu Asp Ile Gly Met Arg Lys Glu Leu I le Met Ser Asp Ala Ala
```

-continued

```
                    100                 105                 110
        Val Glu Gln Arg Arg Ala Leu Ile Lys Arg Lys His Lys Leu Thr Lys
                        115                 120                 125
        Leu Pro Pro Thr Pro Pro Gly Ala Ser Leu Thr Pro Glu Gln Gln His
                        130                 135                 140
        Phe Leu Thr Gln Leu Val Gly Ala His Thr Lys Thr Phe Asp Phe Asn
        145                 150                 155                 160
        Phe Thr Phe Ser Lys Asn Phe Arg Pro Ile Arg Arg Ser Ser Asp Pro
                        165                 170                 175
        Thr Gln Glu Pro Gln Ala Thr Ser Ser Glu Ala Phe Leu Met Leu Pro
                        180                 185                 190
        His Ile Ser Asp Leu Val Thr Tyr Met Ile Lys Gly Ile Ile Ser Phe
                        195                 200                 205
        Ala Lys Met Leu Pro Tyr Phe Lys Ser Leu Asp Ile Glu Asp Gln Ile
                        210                 215                 220
        Ala Leu Leu Lys Gly Ser Val Ala Glu Val Ser Val Ile Arg Phe Asn
        225                 230                 235                 240
        Thr Val Phe Asn Ser Asp Thr Asn Thr Trp Glu Cys Gly Pro Phe Thr
                        245                 250                 255
        Tyr Asp Thr Glu Asp Met Phe Leu Ala Gly Phe Arg Gln Leu Phe Leu
                        260                 265                 270
        Glu Pro Leu Val Arg Ile His Arg Met Met Arg Lys Leu Asn Val Gln
                        275                 280                 285
        Ser Glu Glu Tyr Ala Met Met Ala Ala Leu Ser Ile Phe Ala Ser Tyr
                        290                 295                 300
        Arg Pro Gly Val Cys Asp Trp Glu Lys Ile Gln Lys Leu Gln Glu His
        305                 310                 315                 320
        Ile Ala Leu Thr Leu Lys Asp Phe Ile Asp Ser Gln Arg Pro Pro Ser
                        325                 330                 335
        Pro Gln Asn Arg Leu Leu Tyr Pro Lys Ile Met Glu Cys Leu Thr Glu
                        340                 345                 350
        Leu Arg Thr Val Asn Asp Ile His Ser Lys Gln Leu Leu Glu Ile Trp
                        355                 360                 365
        Asp Ile Gln Pro Asp Ala Thr Pro Leu Met Arg Glu Val Phe Gly Ser
                        370                 375                 380
        Pro Glu
        385

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: both
        (D) TOPOLOGY: linear

(ii) MOLECULE TYPE: DNA (genomic)

(xi) SEQUENCE DESCRIPTION: SEQ ID NO:3:

AGTTCATGAG AGTTCA                                                    16
```